United States Patent
Nomura et al.

(10) Patent No.: US 12,391,649 B2
(45) Date of Patent: Aug. 19, 2025

(54) METHOD FOR PRODUCING DIFLUOROMETHYL-SUBSTITUTED AROMATIC HETEROCYCLIC COMPOUND

(71) Applicant: AGC Inc., Tokyo (JP)

(72) Inventors: Yoshitaka Nomura, Tokyo (JP); Eiichiro Anraku, Tokyo (JP)

(73) Assignee: AGC Inc., Tokyo (JP)

( * ) Notice: Subject to any disclaimer, the term of this patent is extended or adjusted under 35 U.S.C. 154(b) by 572 days.

(21) Appl. No.: 17/815,064

(22) Filed: Jul. 26, 2022

(65) Prior Publication Data

US 2022/0380313 A1 Dec. 1, 2022

Related U.S. Application Data

(63) Continuation of application No. PCT/JP2021/003821, filed on Feb. 3, 2021.

(30) Foreign Application Priority Data

Feb. 6, 2020 (JP) ................. 2020-019210

(51) Int. Cl.
| | |
|---|---|
| C07D 215/12 | (2006.01) |
| C07D 213/26 | (2006.01) |
| C07D 213/84 | (2006.01) |
| C07D 215/48 | (2006.01) |
| C07D 233/70 | (2006.01) |
| C07D 237/30 | (2006.01) |
| C07D 241/42 | (2006.01) |
| C07D 277/64 | (2006.01) |

(52) U.S. Cl.
CPC ......... *C07D 215/12* (2013.01); *C07D 213/26* (2013.01); *C07D 213/84* (2013.01); *C07D 215/48* (2013.01); *C07D 233/70* (2013.01); *C07D 237/30* (2013.01); *C07D 241/42* (2013.01); *C07D 277/64* (2013.01)

(58) Field of Classification Search
CPC .. C07D 215/12; C07D 213/26; C07D 213/84; C07D 215/48; C07D 233/70; C07D 237/30; C07D 241/42; C07D 277/64; C07D 215/04; C07D 233/64
See application file for complete search history.

(56) References Cited

FOREIGN PATENT DOCUMENTS

JP 2012-167047 A 9/2012

OTHER PUBLICATIONS

International Search Report issued Mar. 16, 2021 in PCT/JP2021/003821, filed on Feb. 3, 2021 2 pages.
Loska et al., "Simple Method for the Introduction of Tetrafluoroethyl Substituents into Nitrogen Heterocycles", Mendeleev Communications, vol. 16, No. 3, 2006, 3 Pages, pp. 161-163.
Loska et al., "New Synthesis of 2-Heterarylperfluoropropionic Acids Derivatives by Reaction of Azine N-Oxides with Hexafluoropropene", Chem. Eur. J., vol. 14, 2008, 13 Pages, pp. 2577-2589.
Loska et al., "Synthesis of Alkyl Aryl(heteroaryl)acetates from N-Oxides, 1,1-Difluorostyrenes, and Alcohols", Organic Letters, vol. 15, No. 22, 2013, 4 Pages, pp. 5706-5709.
Mailey et al., "Fluoroalkylpyridines. A Novel Rearrangement", The Journal of Organic Chemistry, vol. 33, No. 8, Aug. 1968, 2 Pages, pp. 3343-334.

*Primary Examiner* — Laura L Stockton
(74) *Attorney, Agent, or Firm* — Oblon, McClelland, Maier & Neustadt, L.L.P.

(57) ABSTRACT

A method for a high yield production of a difluoromethyl-substituted aromatic heterocyclic compound having a partial structure represented by formula (II), which includes reacting an N-oxido aromatic heterocyclic compound having a partial structure represented by formula (I) with tetrafluoroethylene in a solvent selected from an aromatic hydrocarbon solvent, an ester solvent, and an ether solvent.

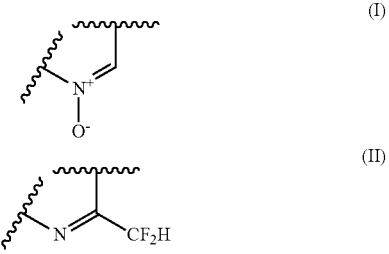

9 Claims, No Drawings

METHOD FOR PRODUCING DIFLUOROMETHYL-SUBSTITUTED AROMATIC HETEROCYCLIC COMPOUND

CROSS-REFERENCE TO RELATED APPLICATIONS

This application is a Continuation of PCT/JP2021/003821, filed on Feb. 3, 2021, and claims priority to Japanese Patent Application No. 2020-019210, filed on Feb. 6, 2020, the entire contents of which are incorporated herein by reference.

TECHNICAL FIELD

The present invention relates to a method for producing difluoromethyl-substituted aromatic heterocyclic compounds.

BACKGROUND ART

Fluorine-containing alkyl group-substituted aromatic heterocyclic compounds, especially difluoromethyl-substituted aromatic heterocyclic compounds are useful as synthetic intermediates for pharmaceutical or agrochemical products.

The following methods are known as methods for producing fluorine-containing alkyl group-substituted aromatic heterocyclic compounds:
a method of reacting quinoline N-oxide with hexafluoropropene ($CF_2$=$CFCF_3$) in N,N-dimethylformamide and water at room temperature in one or two steps to produce 2-(1,2,2,2-tetrafluoroethyl)quinoline (Non-Patent Document 1, Scheme 5); and
a method of reacting quinoline N-oxide with hexafluoropropene ($CF_2$=$CFCF_3$) in N,N-dimethylformamide at room temperature to produce 2-(1,2,2,2-tetrafluoroethyl) quinoline (Non-Patent Document 2, Scheme 1 and Table 1).

However, none of the documents describe productions of difluoromethyl-substituted aromatic heterocyclic compounds or reactions with tetrafluoroethylene ($CF_2$=$CF_2$).

DOCUMENT LIST

Non-Patent Document

Non-Patent Document 1: Chem. Eur. J. 2008, vol. 14, pp 2577-2589
Non-Patent Document 2: Mendeleev Commun. 2006, pp 161-163

SUMMARY OF THE INVENTION

Problems to be Solved by the Invention

The aim of the present invention is to provide a method capable of easily and inexpensively producing difluoromethyl-substituted aromatic heterocyclic compounds in good yield.

Means of Solving the Problems

The present inventors have conducted intensive studies in an attempt to solve the above-mentioned problems and found that by reacting an N-oxido aromatic heterocyclic compound having a partial structure represented by the following formula (I) with tetrafluoroethylene in a specific solvent, a difluoromethyl-substituted aromatic heterocyclic compound having a partial structure represented by the following formula (II) with few by-products can be easily and inexpensively produced in one step, in good yield, which resulted in the completion of the present invention.

Accordingly, the present invention provides the following.

[1] A method for producing a difluoromethyl-substituted aromatic heterocyclic compound having a partial structure represented by the formula (II):

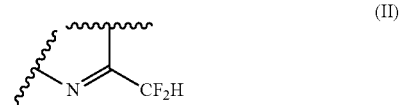 [SMILES: */N=C(\*)C(F)F]

(hereinafter, to be referred to as difluoromethyl-substituted aromatic heterocyclic compound (II)), which comprises reacting an N-oxido aromatic heterocyclic compound having a partial structure represented by the formula (I):

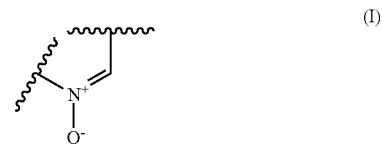 [SMILES: */C=[N+](\*)[O-]]

(hereinafter, to be referred to as N-oxido aromatic heterocyclic compound (I)) with tetrafluoroethylene, in a solvent selected from an aromatic hydrocarbon solvent, an ester solvent and an ether solvent.

[2] The method according to the above [1], wherein the reaction is carried out at temperature in the range of 100 to 300° C.

[3] The method according to the above [1] or [2], wherein the reaction is carried out under pressure in the range of 0.1 to 10.0 MPa.

[4] The method according to any of the above [1] to [3], wherein the reaction is carried out in the presence of a buffer solution with pH 5.0 to 8.0.

[5] The method according to any of the above [1] to [4], wherein the N-oxido aromatic heterocyclic compound having the partial structure represented by the formula (I) is an N-oxido aromatic heterocyclic compound represented by the formula (IA) or (IB):

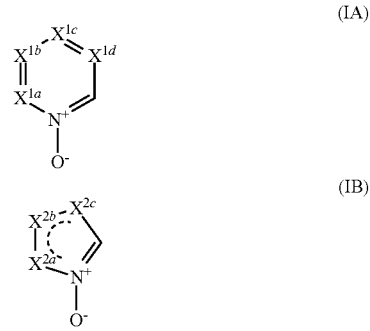

wherein
$X^{1a}$ is $CR^{1a}$ or N;
$X^{1b}$ is $CR^{1b}$ or N;

$X^{1c}$ is $CR^{1c}$ or N;
$X^{1d}$ is $CR^{1d}$ or N;
$R^{1a}$, $R^{1b}$, $R^{1c}$ and $R^{1d}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group, or $R^{1a}$ and $R^{1b}$, $R^{1b}$ and $R^{1c}$, or $R^{1c}$ and $R^{1d}$ are optionally taken together to form a $C_{6-10}$ arene optionally substituted by substituent(s) selected from a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group;
$X^{2a}$ is $CR^{2a}$, N, $NR^{2a}$, S or O;
$X^{2b}$ is $CR^{2b}$ or N;
$X^{2c}$ is $CR^{2c}$, N, $NR^{2c}$, S or O; and
$R^{2a}$, $R^{2b}$ and $R^{2c}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group, or $R^{2a}$ and $R^{2b}$, or $R^{2b}$ and $R^{2c}$ are optionally taken together to form a $C_{6-10}$ arene optionally substituted by substituent(s) selected from a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group (hereinafter, to be referred to as N-oxido aromatic heterocyclic compound (IA) or (IB)).

The method according to the above [5], wherein the N-oxido aromatic heterocyclic compound having the partial structure represented by the formula (I) is represented by the formula (IA), and $R^{1a}$ and $R^{1b}$, $R^{1b}$ and $R^{1c}$, or $R^{1c}$ and $R^{1d}$ in the formula are taken together to form a $C_{6-10}$ arene optionally substituted by substituent(s) selected from a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group.

[7] The method according to the above [5], wherein the N-oxido aromatic heterocyclic compound having the partial structure represented by the formula (I) is represented by the formula (IA), and $R^{1a}$, $R^{1b}$, $R^{1c}$ and $R^{1d}$ in the formula are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group.

[8] The method according to the above [5], wherein the N-oxido aromatic heterocyclic compound having the partial structure represented by the formula (I) is represented by the formula (IB), and $R^{2a}$ and $R^{2b}$, or $R^{2b}$ and $R^{2c}$ in the formula are taken together to form a $C_{6-10}$ arene optionally substituted by substituent(s) selected from a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group.

[9] The method according to the above [5], wherein the N-oxido aromatic heterocyclic compound having the partial structure represented by the formula (I) is represented by the formula (IB), and $R^{2a}$, $R^{2b}$ and $R^{2c}$ in the formula are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group.

Effect of the Invention

According to the present invention, by an easy and inexpensive method of flowing tetrafluoroethylene into N-oxido aromatic heterocyclic compound (I) in a specific solvent, difluoromethyl-substituted aromatic heterocyclic compound (II) with few by-products can be produced in one step, in good yield.

DESCRIPTION OF EMBODIMENTS

Hereinafter, the definitions of the groups used herein will be described in detail. Unless otherwise specified, the groups have the following definitions.

As used herein, the compound represented by the formula is indicated by adding the formula number to the "Compound". For example, the compound represented by the formula (1) is indicated as "Compound (1)".

As used herein, the numerical range represented by "to" or "-" means a numerical range in which the numbers before and after "to" or "-" are the lower and upper limits.

As used herein, when the name of arbitrary group is given the element symbol "C" and a numerical range by numbers before and after "-", it means that the group has an integer number of carbon atoms whose the lower and upper limits are the numbers before and after the "-". For example, an alkyl group having 1 to 3 carbon atoms may be referred to as a "$C_{1-3}$ alkyl group", which indicates each of —$CH_3$, —$C_2H_5$, —$C_3H_7$ and the like. The same applies to other groups.

As used herein, the "halogen atom" means a fluorine atom, a chlorine atom, a bromine atom or an iodine atom.

As used herein, the "$C_{1-6}$ alkyl group" means a linear or branched saturated hydrocarbon group having 1 to 6 carbon atoms. Examples of the "$C_{1-6}$ alkyl group" include methyl, ethyl, propyl, isopropyl, butyl, isobutyl, sec-butyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl and the like. The preferred is a $C_{1-4}$ alkyl group.

As used herein, the "$C_{1-4}$ alkyl group" means a linear or branched saturated hydrocarbon group having 1 to 4 carbon atoms. Examples of the "$C_{1-4}$ alkyl group" include methyl, ethyl, propyl, isopropyl, butyl, isobutyl, sec-butyl and tert-butyl.

As used herein, the "$C_{1-6}$ alkoxy group" means a group represented by the formula $R^{11}O$— wherein $R^{11}$ is a $C_{1-6}$ alkyl group. Examples of the "$C_{1-6}$ alkoxy group" include methoxy, ethoxy, propoxy, isopropoxy, butyloxy, isobutyloxy, sec-butyloxy, tert-butyloxy, pentyloxy, hexyloxy and the like. The preferred is a $C_{1-4}$ alkoxy group.

As used herein, the "$C_{1-6}$ haloalkyl group" means a group in which the one or more hydrogen atoms of the "$C_{1-6}$ alkyl group" are replaced with halogen atoms. Examples of the "$C_{1-6}$ haloalkyl group" include fluoromethyl, 2-fluoroethyl, 3-fluoropropyl, 4-fluorobutyl, trifluoromethyl, difluoromethyl, perfluoroethyl, perfluoropropyl, chloromethyl, 2-chloroethyl, bromomethyl, 2-bromoethyl, iodomethyl, 2-iodoethyl and the like. The preferred is trifluoromethyl.

As used herein, the "$C_{1-6}$ haloalkoxy group" means a group in which the one or more hydrogen atoms of the "$C_{1-6}$ alkoxy group" are replaced with halogen atoms. Examples of the "$C_{1-6}$ haloalkoxy group" include bromomethoxy, 2-bromoethoxy, 3-bromopropoxy, 4-bromobutoxy, iodomethoxy, 2-iodoethoxy, 3-iodopropoxy, 4-iodobutoxy, fluoromethoxy, 2-fluoroethoxy, 3-fluoropropoxy, 4-fluorobutoxy, tribromomethoxy, trichloromethoxy, trifluoromethoxy, difluoromethoxy, perfluoroethoxy, perfluoropropoxy, perfluoroisopropoxy, 1,1,2,2-tetrafluoroethoxy and 2-chloro-1,1,2-trifluoroethoxy.

As used herein, the "$C_{1-6}$ alkylsulfanyl group" means a group represented by the formula $R^{11}S$— wherein $R^{11}$ is a $C_{1-6}$ alkyl group. Examples of the "$C_{1-6}$ alkylsulfanyl group" include methylsulfanyl, ethylsulfanyl, propylsulfanyl, isopropylsulfanyl, butylsulfanyl, isobutylsulfanyl, sec-butylsulfanyl, tert-butylsulfanyl, pentylsulfanyl, hexylsulfanyl and the like. The preferred is a $C_{1-4}$ sulfanyl group.

As used herein, the "mono-$C_{1-6}$ alkylamino group" means a group represented by the formula $R^{11}NH$— wherein $R^{11}$ is a $C_{1-6}$ alkyl group. Examples of the "mono-$C_{1-6}$ alkylamino group" include methylamino, ethylamino, propylamino, isopropylamino, butylamino, isobutylamino, sec-butylamino, tert-butylamino, pentylamino, hexylamino and the like. The preferred is a mono-$C_{1-4}$ alkylamino group.

As used herein, the "di-$C_{1-6}$ alkylamino group" means a group represented by the formula $R^{11}{}_2N$— wherein the two $R^{11}$ are each independently a $C_{1-6}$ alkyl group. Examples of the "di-$C_{1-6}$ alkylamino group" include dimethylamino, diethylamino, N-ethyl-N-methylamino, dipropylamino, diisopropylamino, dibutylamino, diisobutylamino, disec-butylamino, ditert-butylamino, dipentylamino, dihexylamino and the like. The preferred is a di-$C_{1-4}$ alkylamino group.

As used herein, the "$C_{1-6}$ alkoxy-carbonyl group" means a group represented by the formula $R^{11}OC(=O)$— wherein $R^{11}$ is a $C_{1-6}$ alkyl group. Examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl and the like. The preferred is a $C_{1-4}$ alkoxy-carbonyl group.

As used herein, the "$C_{6-10}$ aryl group" means a hydrocarbon group having 6 to 10 carbon atoms and having aromaticity. Examples of the "$C_{6-10}$ aryl group" include phenyl, 1-naphthyl and 2-naphthyl. The preferred is phenyl.

As used herein, the "$C_{7-16}$ aralkyl group" means the "$C_{1-6}$ alkyl group" substituted by the "$C_{6-10}$ aryl group". Examples of the "$C_{7-16}$ aralkyl group" include benzyl, 1-phenylethyl, 2-phenylethyl, 3-phenylpropyl, 4-phenylbutyl, (1-naphthyl)methyl, (2-naphthyl)methyl and the like. The preferred is benzyl.

As used herein, the "$C_{6-10}$ arene" means a hydrocarbon ring having 6 to 10 carbon atoms and having aromaticity. Examples of the "$C_{6-10}$ arene" include benzene and naphthalene. The preferred is benzene.

As used herein, Examples of the substituent of the "optionally substituted $C_{6-10}$ arene" include a halogen atom, a cyano group, a $C_{1-6}$ alkyl group, a hydroxy group, a $C_{1-6}$ alkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group.

Hereinafter, the production method of the present invention is explained.

In the present invention, difluoromethyl-substituted aromatic heterocyclic compound (II) is produced by reacting N-oxido aromatic heterocyclic compound (I) with tetrafluoroethylene, in a solvent selected from an aromatic hydrocarbon solvent, an ester solvent and an ether solvent. The reaction mechanism is as follows, for example, if a proton source is present and it is water.

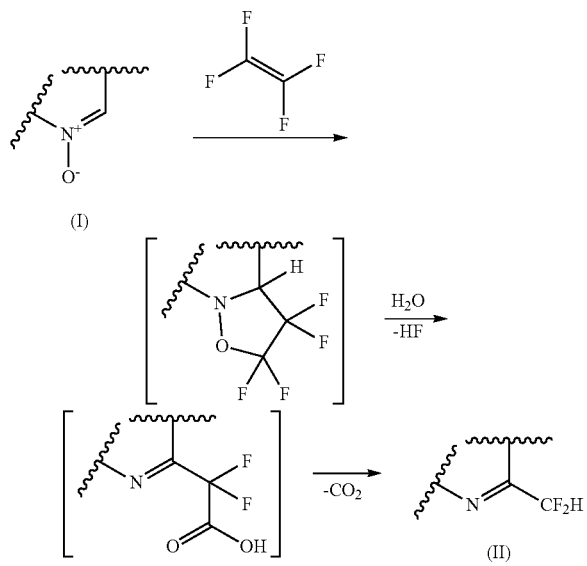

Specific examples of N-oxido aromatic heterocyclic compound (I) include the following N-oxido aromatic heterocyclic compounds (IA) and (IB):

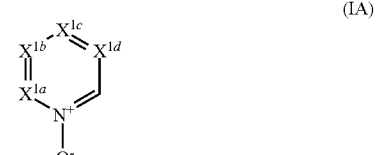

(IA)

(IB)

wherein
$X^{1a}$ is $CR^{1a}$ or N;
$X^{1b}$ is $CR^{1b}$ or N;
$X^{1c}$ is $CR^{1c}$ or N;

$X^{1d}$ is $CR^{1d}$ or N;

$R^{1a}$, $R^{1b}$, $R^{1c}$ and $R^{1d}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group, or $R^{1a}$ and $R^{1b}$, $R^{1b}$ and $R^{1c}$, or $R^{1c}$ and $R^{1d}$ are optionally taken together to form a $C_{6-10}$ arene optionally substituted by substituent(s) selected from a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group;

$X^{2a}$ is $CR^{2a}$, N, $NR^{2a}$, S or O;

$X^{2b}$ is $CR^{2b}$ or N;

$X^{2c}$ is $CR^{2c}$, N, $NR^{2c}$, S or O; and $R^{2a}$, $R^{2b}$ and $R^{2c}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group, or $R^{2a}$ and $R^{2b}$, or $R^{2b}$ and $R^{2c}$ are optionally taken together to form a $C_{6-10}$ arene optionally substituted by substituent(s) selected from a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group.

$R^{1a}$, $R^{1b}$, $R^{1c}$ and $R^{1d}$ are preferably each independently a hydrogen atom, a cyano group or a $C_{1-6}$ alkyl group, or $R^{1a}$ and $R^{1b}$, $R^{1b}$ and $R^{1c}$, or $R^{1c}$ and $R^{1d}$ are optionally taken together to form a $C_{6-10}$ arene optionally substituted by $C_{1-6}$ alkoxy-carbonyl group(s).

$R^{2a}$, $R^{2b}$ and $R^{2c}$ are preferably each independently a hydrogen atom, a $C_{1-6}$ alkyl group or a $C_{7-16}$ aralkyl group, or $R^{2a}$ and $R^{2b}$, or $R^{2b}$ and $R^{2c}$ are optionally taken together to form a $C_{6-10}$ arene.

In the formula (IB), one of the bond $R^{2a}$-$R^{2b}$ and the bond $R^{2b}$-$R^{2c}$ is a single bond, and the other is a double bond. Provided that when $X^{2a}$ is S or O, then the bond $R^{2a}$-$R^{2b}$ is a single bond, and the bond $R^{2b}$-$R^{2c}$ is a double bond. Also, provided that when $X^{2c}$ is S or O, then the bond $R^{2a}$-$R^{2b}$ is a double bond, and the bond $R^{2b}$-$R^{2c}$ is a single bond.

Specific examples of N-oxido aromatic heterocyclic compound (IA) include the following N-oxido aromatic heterocyclic compounds (IA-a)-(IA-e).

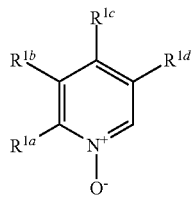
(IA-a)

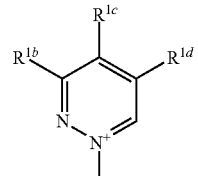
(IA-b)

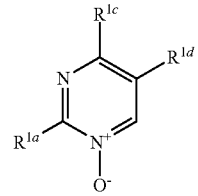
(IA-c)

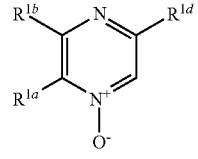
(IA-d)

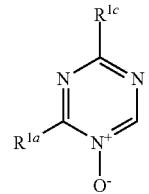
(IA-e)

wherein each symbol in the formula is as defined above.

Among them, the preferred are (IA-a), (IA-b) and (IA-d).

Preferable specific examples of N-oxido aromatic heterocyclic compound (IA) include the following compounds.

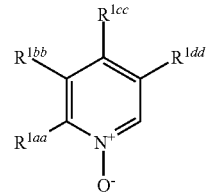
(IA-a1)

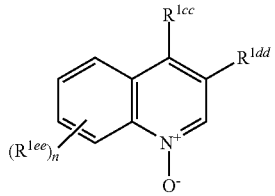
(IA-a2)

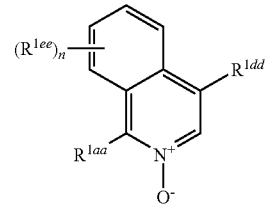
(IA-a3)

-continued

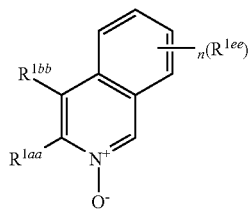
(IA-a4)

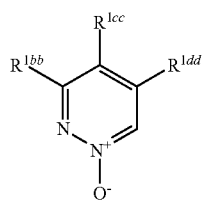
(IA-b1)

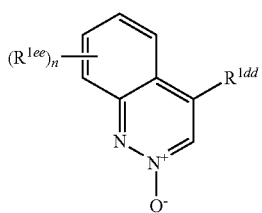
(IA-b2)

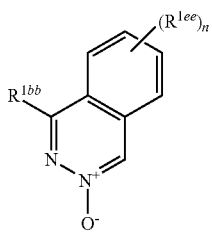
(IA-b3)

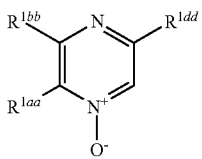
(IA-d1)

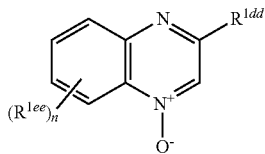
(IA-d2)

wherein $R^{1aa}$, $R^{1bb}$, $R^{1cc}$ and $R^{1dd}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group;

$R^{1ee}$ in the number of n are each independently a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group; and n is an integer of 0 to 4.

$R^{1aa}$, $R^{1bb}$, $R^{1cc}$ and $R^{1dd}$ are preferably each independently a hydrogen atom, a cyano group or a $C_{1-6}$ alkyl group;

$R^{1ee}$ in the number of n are preferably each independently a $C_{1-6}$ alkoxy-carbonyl group; and n is 0 or 1.

Specific examples of N-oxido aromatic heterocyclic compound (IB) include the following N-oxido aromatic heterocyclic compounds (IB-a)-(IB-ff).

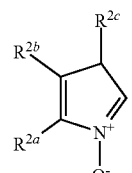
(IB-a)

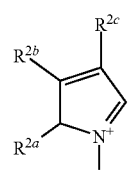
(IB-b)

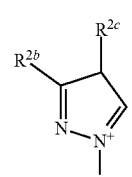
(IB-c)

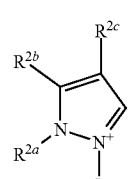
(IB-d)

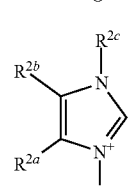
(IB-e)

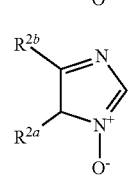
(IB-f)

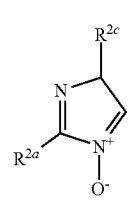
(IB-g)

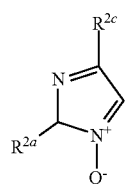 (IB-h)
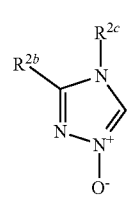 (IB-i)
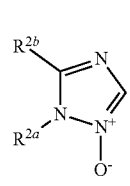 (IB-j)
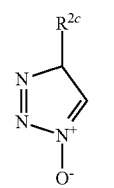 (IB-k)
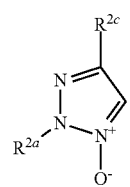 (IB-l)
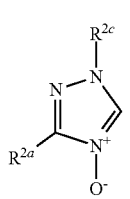 (IB-m)
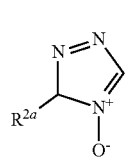 (IB-n)
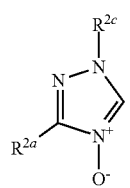 (IB-o)
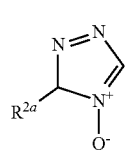 (IB-p)
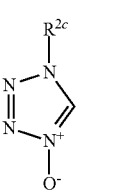 (IB-q)
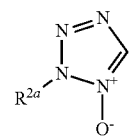 (IB-r)
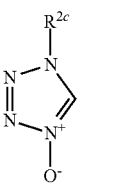 (IB-s)
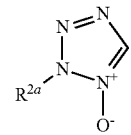 (IB-t)
 (IB-u)
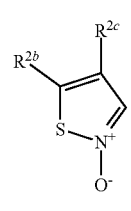 (IB-v)
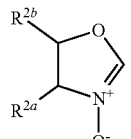 (IB-w)
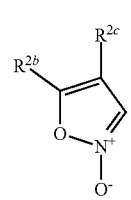 (IB-x)
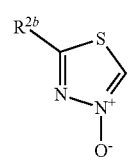 (IB-y)

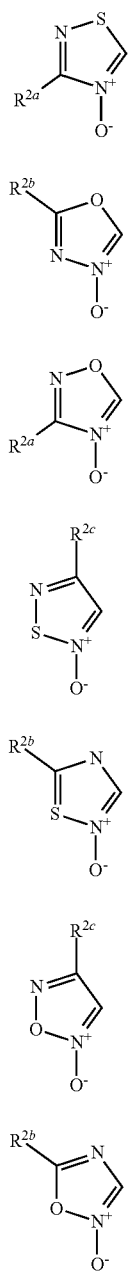
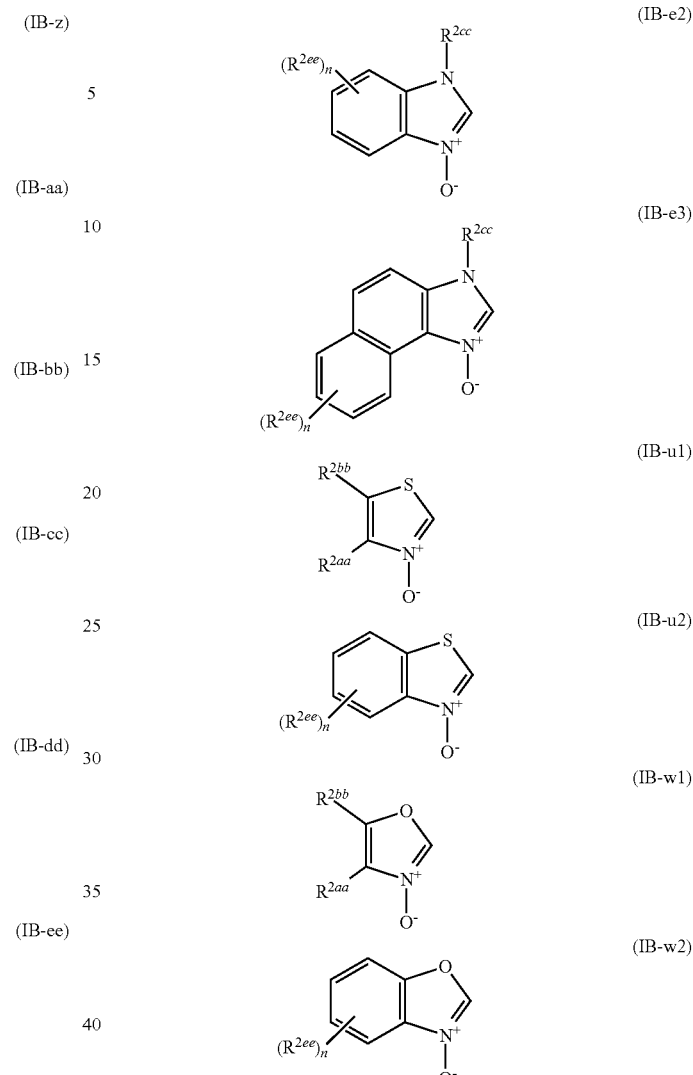

wherein each symbol in the formula is as defined above.

Among them, the preferred are (IB-e), (IB-u) and (IB-w).

Preferable specific examples of N-oxido aromatic heterocyclic compound (IB) include the following compounds.

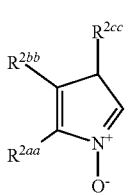

wherein
$R^{2aa}$, $R^{2bb}$ and $R^{2cc}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group;
$R^{2ee}$ in the number of n are each independently a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group; and
n is an integer of 0 to 4.

$R^{2aa}$, $R^{2bb}$ and $R^{2cc}$ are preferably each independently a hydrogen atom, a $C_{1-6}$ alkyl group or a $C_{7-16}$ aralkyl group; and n is 0.

N-Oxido aromatic heterocyclic compound (I) may be commercially available, or can be produced according to a method known per se.

Tetrafluoroethylene ($CF_2=CF_2$) can be produced according to a known method. Since tetrafluoroethylene is in a gaseous state at room temperature under atmospheric pressure, it is added to the reaction system by inflow. In this case, tetrafluoroethylene diluted with nitrogen gas may be flowed into the reaction system. The amount of the tetrafluoroethylene to be used is generally 1 to 100 mol, preferably 1 to 10 mol, per 1 mol of N-oxido aromatic heterocyclic compound (I).

The reaction is carried out using a proton source, and the proton source may be present from the start of the reaction, or added during the reaction, or it may be a compound generated in the reaction process (e.g., hydrogen fluoride). From the aspect of the reaction rate, the proton source is preferably present from the start of the reaction.

Examples of the proton source include inorganic acids, organic acids, water and the like, specifically, hydrogen fluoride, hydrogen chloride, ammonium salts, water, buffer solutions and the like. Among them, the preferred are water and hydrogen fluoride. Water can be molecules hydrated in the raw material N-oxido aromatic heterocyclic compound (I). Hydrogen fluoride can be molecules generated in the reaction process.

The amount of the proton source to be used can be appropriately selected. When the proton source is, for example, water or a buffer solution as described above, the amount is preferably 0.05 to 0.5 times the volume of the solvent described below. When the proton source is, for example, hydrated water molecules as described above, the amount is preferably 1 to 10 mol, per 1 mol of N-oxido aromatic heterocyclic compound (I). When the proton source is, for example, hydrogen fluoride molecules generated in the reaction process, as described above, the amount is preferably 1 mol, per 1 mol of N-oxido aromatic heterocyclic compound (I).

The reaction may be carried out in the presence of an additive.

The reaction is carried out in a solvent selected from an aromatic hydrocarbon solvent, an ester solvent and an ether solvent. The use of such solvent allows for good dissolution of tetrafluoroethylene and thus the production of difluoromethyl-substituted aromatic heterocyclic compounds (II) with few by-products in good yield.

Examples of the aromatic hydrocarbon solvent include toluene, xylene, nitrobenzene and the like.

Examples of the ester solvent include butyl acetate, octyl acetate and the like.

Examples of the ether solvent include dibutyl ether, cyclopentyl methyl ether and the like.

The solvent used in the reaction is preferably a solvent having a boiling point of 80° C. or higher, more preferably a solvent having a boiling point of 100° C. or higher, particularly preferably a solvent having a boiling point of 110° C. or higher, from the aspect of the reaction temperature. Examples of such solvents include toluene, xylene, nitrobenzene, butyl acetate, octyl acetate, dibutyl ether, cyclopentyl methyl ether and the like. Among them, the preferred are toluene, xylene and butyl acetate.

The amount of the solvent to be used is generally 100 to 1000 times, preferably 100 to 200 times the volume of N-oxido aromatic heterocyclic compound (I).

The reaction may be carried out in a flow system while flowing tetrafluoroethylene into a mixture of N-oxido aromatic heterocyclic compound (I), a proton source and a solvent. Alternatively, the reaction may be carried out in a sealed system after flowing tetrafluoroethylene into a mixture of N-oxido aromatic heterocyclic compound (I), a proton source and a solvent. The reaction is carried out preferably in a sealed system, more preferably under pressure in the range of 0.1 to 100.0 MPa, particularly preferably in the range of 0.1 to 10.0 MPa, from the aspect of the reaction efficiency, yield and reduction of by-products.

When N-oxido aromatic heterocyclic compound (I) is represented by the formula (IA), and $R^{1a}$ and $R^{1b}$, $R^{1b}$ and $R^{1c}$, or $R^{1c}$ and $R^{1d}$ are taken together to form the above $C_{6-10}$ arene, then the reaction is carried out preferably under pressure in the range of 0.1 to 10.0 MPa, more preferably in the range of 0.1 to 1.0 MPa, particularly preferably in the range of 0.1 to 0.5 MPa, from the aspect of ease of the reaction progress and increase in the reaction rate.

On the other hand, when N-oxido aromatic heterocyclic compound (I) is represented by the formula (IA), and does not form the above $C_{6-10}$ arene, then the reaction may be carried out under pressure in the above range. From the aspect of reduce in the reaction time, the reaction may be carried out preferably under pressure in the range of 0.1 to 30.0 MPa, more preferably in the range of 1.5 to 3.0 MPa, particularly preferably in the range of 2.0 to 2.5 MPa.

Prior to the inflow of tetrafluoroethylene, the reaction system is preferably degassed in advance. The reaction is also carried out preferably under nitrogen atmosphere.

The reaction is carried out preferably in the presence of a buffer solution with pH 5.0 to 8.0, more preferably in the presence of a buffer solution with pH 5.0 to 7.0. The use of such buffer solution reduces the formation of by-products and improves the yield. Examples of the buffer solution include phosphate buffer solutions (pH 7.0 to 7.5). For example, in the case of phosphate buffer solutions (pH 7.0-7.5), the amount of the buffer solution to be used is preferably 0.05 to 0.5 times the volume of the above solvent.

The reaction is carried out generally at 100° C. or higher, preferably at temperature in the range of 100 to 300° C.

When N-oxido aromatic heterocyclic compound (I) is represented by the formula (IA), and $R^{1a}$ and $R^{1b}$, $R^{1b}$ and $R^{1c}$, or $R^{1c}$ and $R^{1d}$ are taken together to form the above $C_{6-10}$ arene, then the reaction is carried out preferably at temperature in the range of 100 to 200° C., particularly preferably in the range of 100 to 150° C., from the aspect of ease of the reaction progress.

On the other hand, when N-oxido aromatic heterocyclic compound (I) is represented by the formula (IA), and does not form the above $C_{6-10}$ arene, then the reaction may be carried out at temperature in the above range. From the aspect of ease of the reaction progress, the reaction may be carried out preferably at temperature in the range of 200 to 300° C., particularly preferably in the range of 200 to 250° C.

The reaction time varies depending on the kind of N-oxido aromatic heterocyclic compound (I) and the reaction temperature, and it is generally 12 to 120 hr, preferably 24 to 48 hr.

After the completion of the reaction, the objective difluoromethyl-substituted aromatic heterocyclic compound (II) can be isolated and purified from the reaction mixture according to conventional method, for example, a separation means such as concentration, crystallization, recrystallization, distillation, solvent extraction, fractional distillation, column chromatography and the like.

The container used for the reaction of tetrafluoroethylene and N-oxido aromatic heterocyclic compound (I) is not limited as long as it does not adversely affect the reaction. For example, metal containers and the like can be used. Since olefin in a gaseous state under the reaction condition is handled in the present invention, the use of air-sealing, pressure-resistant containers is preferable. Moreover, since the compound generated as the reaction progresses may become a reaction inhibitor by reacting with the metal of the reaction container, the use of containers lined with resin such as PFA or glass is preferable.

Difluoromethyl-substituted aromatic heterocyclic compound (II) thus obtained is useful as a synthetic intermediate for pharmaceutical or agrochemical products, and can be led to various pharmaceutical or agrochemical products.

EXAMPLES

The present invention is explained in detail in the following by referring to Examples, which are not to be construed as limitative.
[Analysis Method]
The present invention is explained in detail in the following by referring to Examples, which are not to be construed as limitative. Nuclear magnetic resonance spectrum (NMR) was measured using JNM-AL300 manufactured by JEOL Ltd. $^1$H NMR was measured at 300 MHz using tetramethylsilane as standard.

Mass spectrometry (LC-MS) was measured using liquid chromatograph mass spectrum system (LCMS6120B) manufactured by Agilent Technologies. Mass spectrometry (GC-MS) was determined by electron ionization (EI) using gas chromatograph mass spectrometer (GCMS-QP5000V2 or GCMS-QP2010Ultra) manufactured by Shimadzu Corporation.

Example 1

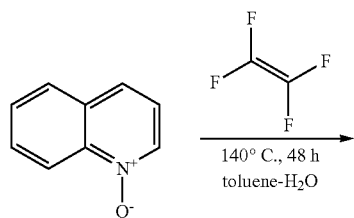

A PFA-lined SUS reactor having a volume of 25 cm$^3$ was charged with toluene (10 ml) and water (1 ml), and the mixture was stirred, and kept at 25° C. Then, quinoline N-oxide (109 mg, 0.751 mmol, Compound 1) was added thereto, and the mixture was degassed under reduced pressure. Tetrafluoroethylene diluted to 50% with nitrogen gas was refilled until the reactor pressure reached 0.1 MPa, and the mixture was kept stirred under heating at 140° C. for 48 hr. By measuring $^1$H-NMR and GC-MS of the crude solution after the completion of the reaction, it was found that Compound 2 was obtained in a yield of 33%.

$^1$H-NMR and GC-MS of the above Compound (2) are shown below.

$^1$H-NMR (CDCl$_3$) δ 8.34 (d, 1H), 8.15 (d, 1H), 7.90 (d, 1H), 7.80 (dd, 1H), 7.74 (d, 1H), 7.65 (dd, 1H), 6.79 (t, 1H)
GC-MS (EI): [M+]=179

Example 2

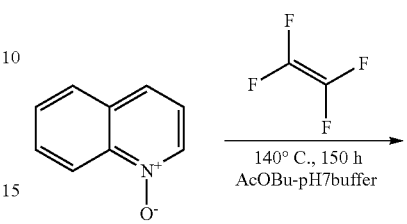

A SUS reactor having a volume of 25 cm$^3$ was charged with butyl acetate (10 ml) and phosphate buffer solution (0.1 mol/l, pH 7.0, 1 ml) prepared from sodium dihydrogen phosphate (NaH$_2$PO$_4$) and disodium hydrogen phosphate (Na$_2$HPO$_4$), and the mixture was stirred, and kept at 25° C. Then, quinoline N-oxide (109 mg, 0.751 mmol, Compound 1) was added thereto, and the mixture was degassed under reduced pressure. Tetrafluoroethylene diluted to 50% with nitrogen gas was refilled until the reactor pressure reached 0.1 MPa, and the mixture was kept stirred under heating at 140° C. for 150 hr. By measuring $^1$H-NMR of the crude solution after the completion of the reaction, it was found that Compound 2 was obtained in a yield of 43%.

Comparative Example 1

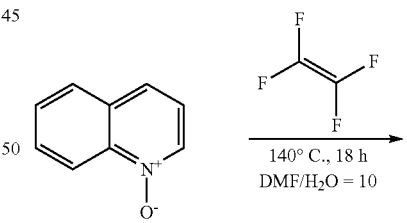

A SUS reactor having a volume of 25 cm$^3$ was charged with DMF (10 ml) and water (1 ml), and the mixture was stirred, and kept at 25° C. Then, quinoline N-oxide (109 mg, 0.751 mmol, Compound 1) was added thereto, and the mixture was degassed under reduced pressure. Tetrafluoroethylene diluted to 50% with nitrogen gas was refilled until the reactor pressure reached 0.1 MPa, and the mixture was kept stirred under heating at 140° C. for 48 hr. By measuring $^1$H-NMR of the crude solution after the completion of the reaction, it was found that Compound 2 was not obtained, instead Compound 3 was obtained in a yield of 56%. The structure of Compound 3 was determined by confirming that its spectrum was consistent with that of Compound 3 purchased from FUJIFILM Wako Chemical Co., Ltd.

Reference Example 1

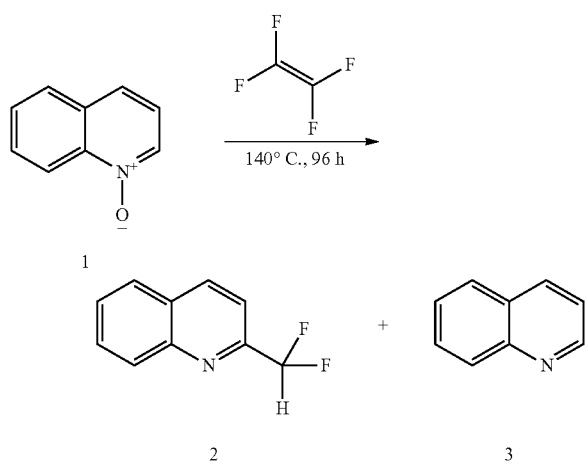

A crude solution containing Compounds 2 and 3 was obtained from Compound 1 in the same procedure as in Example 1, except that the reaction was carried out under solvent-free conditions without toluene and water. By measuring $^1$H-NMR and GC-MS of the crude solution after the completion of the reaction, it was found that Compound 2 was obtained in a yield of 13%.

Example 3

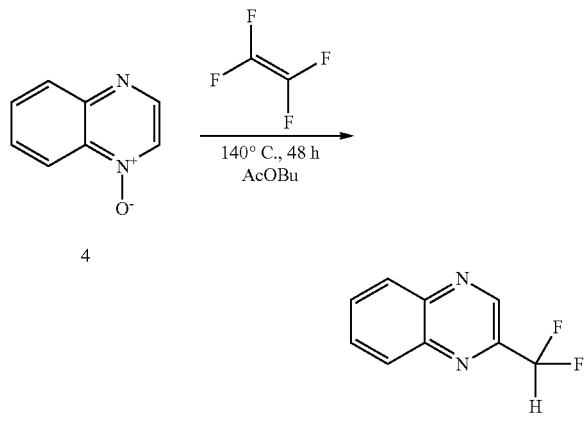

A crude solution containing Compound 5 was obtained from Compound 4 in the same procedure as in Example 1, except that toluene and water were replaced with butyl acetate. By measuring $^1$H-NMR and GC-MS of the crude solution after the completion of the reaction, it was found that Compound 5 was obtained in a yield of 62%. In this Example, the hydrate of Compound 4 was used as a raw material.

$^1$H-NMR and GC-MS of the above Compound (5) are shown below.

$^1$H-NMR (CDCl$_3$) δ 9.19 (s, 1H), 8.14-8.23 (m, 2H), 7.84-7.91 (m, 2H), 6.84 (t, 1H)

GC-MS (EI): [M+]=180

Example 4

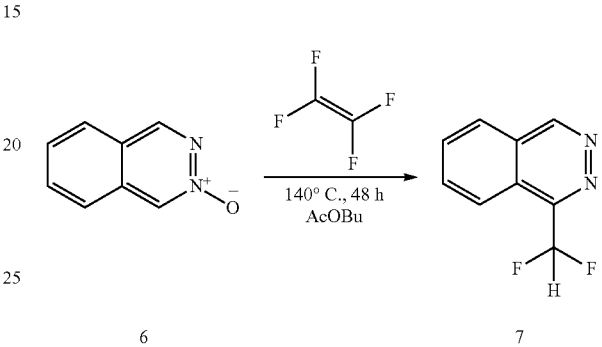

A crude solution containing Compound 7 was obtained from Compound 6 in the same procedure as in Example 1, except that toluene and water were replaced with butyl acetate. By measuring $^1$H-NMR and GC-MS of the crude solution after the completion of the reaction, it was found that Compound 7 was obtained in a yield of 56%. In this Example, the hydrate of Compound 6 was used as a raw material.

$^1$H-NMR and GC-MS of the above Compound (7) are shown below.

$^1$H-NMR (CDCl$_3$) δ 9.62 (s, 1H), 8.22 (m, 2H), 8.08 (m, 2H), 7.28 (t, 1H)

GC-MS (EI): [M+]=180

Example 5

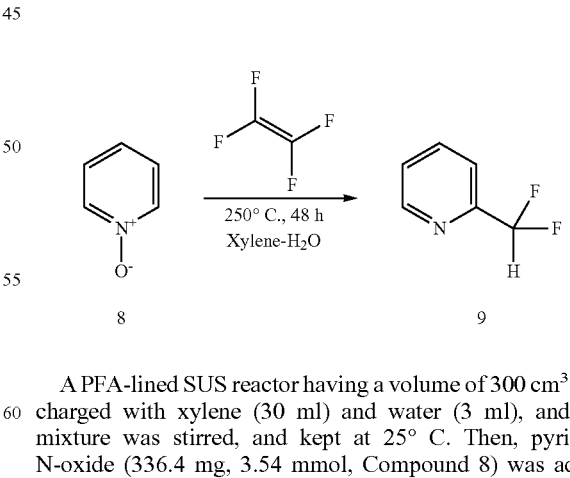

A PFA-lined SUS reactor having a volume of 300 cm$^3$ was charged with xylene (30 ml) and water (3 ml), and the mixture was stirred, and kept at 25° C. Then, pyridine N-oxide (336.4 mg, 3.54 mmol, Compound 8) was added thereto, and the mixture was degassed under freezing. Tetrafluoroethylene diluted to 50% with nitrogen gas was refilled until the reactor pressure reached 0.3 MPa, and the mixture was kept stirred under heating at 250° C. for 8 hr. By measuring GC-MS of the crude solution after the completion of the reaction, it was found that Compound 9 was obtained in a yield of 49%. The structure of Compound 9 was determined by confirming that its spectrum was consistent with that of Compound 9 purchased from FUJI-FILM Wako Chemical Co., Ltd.

GC-MS (EI): [M+]=129

Example 6

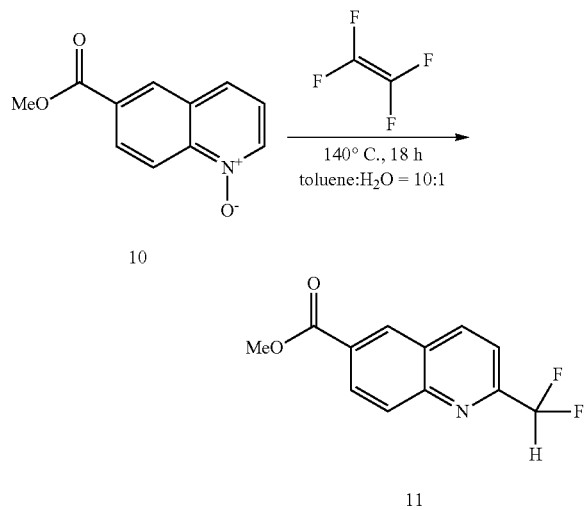

A crude solution containing Compound 11 was obtained from Compound 10 in the same procedure as in Example 1. By measuring $^1$H-NMR and GC-MS of the crude solution after the completion of the reaction, it was found that Compound 11 was obtained in a yield of 78%.

$^1$H-NMR and LC-MS of the above Compound (11) are shown below.

$^1$H-NMR (CDCl$_3$) δ 8.63 (d, 1H), 8.34-8.43 (m, 2H), 8.18 (d, 1H), 7.79 (d, 1H), 6.78 (t, 1H), 4.02 (s, 3H)

LC-MS: [M+1]=238

Example 7

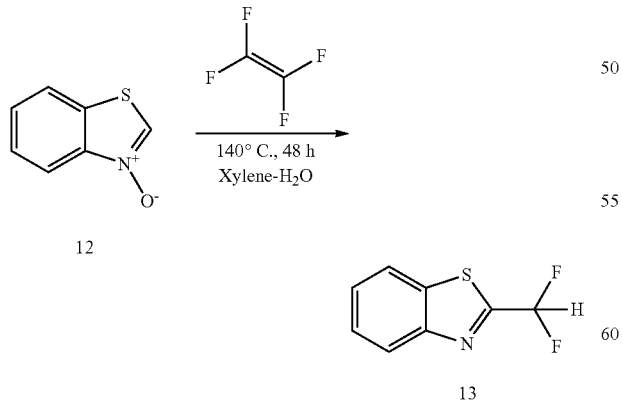

A crude solution containing Compound 13 was obtained from Compound 12 in the same procedure as in Example 1, except that toluene was replaced with xylene. By measuring $^1$H-NMR and GC-MS of the crude solution after the completion of the reaction, it was found that Compound 13 was obtained in a yield of 60%.

$^1$H-NMR and GC-MS of the above Compound (13) are shown below.

$^1$H-NMR (DMSO) δ 7.38-7.70 (m, 3H), 8.20 (m, 1H), 8.26 (m, 1H)

GC-MS (EI): [M+]=186

Example 8

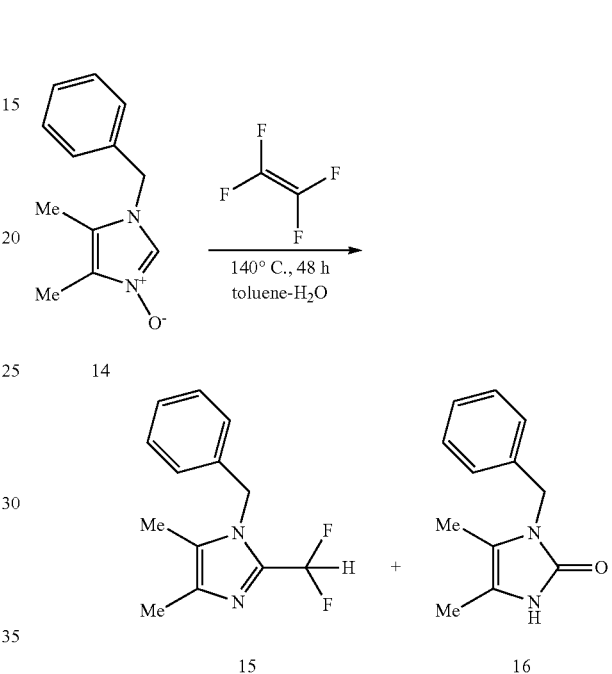

A crude solution containing Compounds 15 and 16 was obtained from Compound 14 in the same procedure as in Example 1. By measuring $^1$H-NMR and GC-MS of the crude solution after the completion of the reaction, it was found that Compound 15 was obtained in a yield of 38%.

$^1$H-NMR and LC-MS of the above Compound (15) are shown below.

$^1$H-NMR (CDCl$_3$) δ 7.27-7.39 (m, 5H), 6.70 (t, J=52.9 Hz, 1H), 5.27 (s, 2H), 2.19 (s, 3H), 1.98 (s, 3H)

LC-MS: [M+1]=237

Example 9

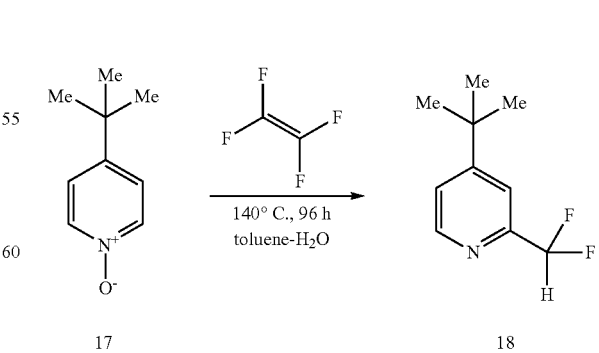

A crude solution containing Compound 18 was obtained from Compound 17 in the same procedure as in Example 1.

By measuring $^1$H-NMR and GC-MS of the crude solution after the completion of the reaction, it was found that Compound 18 was obtained in a yield of 26%.

$^1$H-NMR and GC-MS of the above Compound (18) are shown below.

$^1$H-NMR (CDCl$_3$) δ 8.55 (d, 1H), 7.62 (s, 1H), 7.39 (d, 1H), 6.64 (t, 1H), 1.34 (s, 9H)

GC-MS (EI): [M+]=185

Example 10

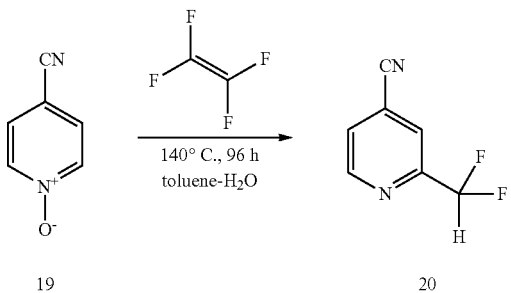 [SMILES: N#Cc1cc[n+]([O-])cc1 ; FC(F)=C(F)F ; N#Cc1ccnc(C(F)F)c1]

19            20

A crude solution containing Compound 20 was obtained from Compound 19 in the same procedure as in Example 1. By measuring $^1$H-NMR and GC-MS of the crude solution after the completion of the reaction, it was found that Compound 20 was obtained in a yield of 20%.

$^1$H-NMR and GC-MS of the above Compound (20) are shown below.

$^1$H-NMR (CDCl$_3$) δ 8.87 (d, 1H), 7.88 (s, 1H), 7.73-7.59 (m, 1H), 6.68 (t, 1H)

GC-MS (EI): [M+]=154

INDUSTRIAL APPLICABILITY

According to the present invention, by an easy and inexpensive method of flowing tetrafluoroethylene into N-oxido aromatic heterocyclic compound (I) in a specific solvent, difluoromethyl-substituted aromatic heterocyclic compound (II) with few by-products can be produced in one step, in good yield.

This application is based on patent application No. 2020-019210 filed on Feb. 6, 2020 in Japan, the contents of which are encompassed in full herein.

The invention claimed is:

1. A method for producing a difluoromethyl-substituted aromatic heterocyclic compound having a partial structure represented by formula (II) comprising:
reacting an N-oxido aromatic heterocyclic compound having a partial structure represented by formula (I) with tetrafluoroethylene in at least one solvent selected from the group consisting of an aromatic hydrocarbon, an ester, and an ether

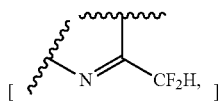 (II)

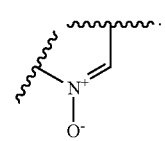 (I)

2. The method according to claim 1, wherein the reacting is carried out at a temperature in the range of 100 to 300° C.

3. The method according to claim 1, wherein the reacting is carried out under pressure in the range of 0.1 to 10.0 MPa.

4. The method according to claim 1, wherein the reacting is carried out in the presence of a buffer solution with pH 5.0 to 8.0.

5. The method according to claim 1, wherein the N-oxido aromatic heterocyclic compound having the partial structure represented by formula (I) is an N-oxido aromatic heterocyclic compound represented by formula (IA) or (IB):

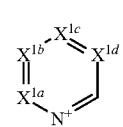 (IA)

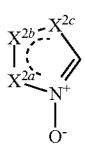 (IB)

wherein
$X^{1a}$ is $CR^{1a}$ or N;
$X^{1b}$ is $CR^{1b}$ or N;
$X^{1c}$ is $CR^{1c}$ or N;
$X^{1d}$ is $CR^{1d}$ or N; and
$R^{1a}$, $R^{1b}$, $R^{1c}$ and $R^{1d}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxycarbonyl group, a $C_{6-10}$ aryl group or a $C_{7-16}$ aralkyl group, or $R^{1a}$ and $R^{1b}$, $R^{1b}$ and $R^{1c}$, or $R^{1c}$ and $R^{1d}$ are optionally taken together to form a $C_{6-10}$ arene optionally substituted by at least one substituent selected from the group consisting of a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group, and a $C_{7-16}$ aralkyl group;
wherein
$X^{2a}$ is $CR^{2a}$, N, $NR^{2a}$, S or O;
$X^{2b}$ is $CR^{2b}$ or N;
$X^{2c}$ is $CR^{2c}$, N, $NR^{2c}$, S or O; and
$R^{2a}$, $R^{2b}$ and $R^{2c}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group, or $R^{2a}$ and $R^{2b}$, or $R^{2b}$ and $R^{2c}$ are optionally taken together to form a $C_{6-10}$ arene optionally substituted by at least one substituent selected from the group consisting of a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group, and a $C_{7-16}$ aralkyl group.

6. The method according to claim 5, wherein the N-oxido aromatic heterocyclic compound having the partial structure represented by formula (I) is a compound having the formula (IA), and $R^{1a}$ and $R^{1b}$, $R^{1b}$ and $R^{1c}$, or $R^{1c}$ and $R^{1d}$ are taken together to form a $C_{6-10}$ arene optionally substituted by at least one substituent selected from the group consisting of a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group, and a $C_{7-16}$ aralkyl group.

7. The method according to claim 5, wherein the N-oxido aromatic heterocyclic compound having the partial structure represented by formula (I) is a compound having the formula (IA), and $R^{1a}$, $R^{1b}$, $R^{1c}$ and $R^{1d}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group.

8. The method according to claim 5, wherein the N-oxido aromatic heterocyclic compound having the partial structure represented by formula (I) is a compound having the formula (IB), and $R^{2a}$ and $R^{2b}$, or $R^{2b}$ and $R^{2c}$ are taken together to form a $C_{6-10}$ arene optionally substituted by at least one substituent selected from the group consisting of a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group, and a $C_{7-16}$ aralkyl group.

9. The method according to claim 5, wherein the N-oxido aromatic heterocyclic compound having the partial structure represented by formula (I) is a compound having the formula (IB), and $R^{2a}$, $R^{2b}$ and $R^{2c}$ in the are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group.

\* \* \* \* \*